United States Patent
Jett et al.

(10) Patent No.: US 6,869,511 B2
(45) Date of Patent: Mar. 22, 2005

(54) CERAMIC ELECTROCHEMICAL CORROSION POTENTIAL SENSOR PROBE WITH INCREASED LIFETIME

(75) Inventors: Robert Jett, Twinsburg, OH (US); Lucas Clarke, North Canton, OH (US)

(73) Assignee: General Electric Company, Schenectady, NY (US)

( * ) Notice: Subject to any disclaimer, the term of this patent is extended or adjusted under 35 U.S.C. 154(b) by 271 days.

(21) Appl. No.: 10/218,522

(22) Filed: Aug. 15, 2002

(65) Prior Publication Data

US 2004/0031681 A1 Feb. 19, 2004

(51) Int. Cl.$^7$ ............................................. G01N 27/406
(52) U.S. Cl. ...................................... 204/404; 204/422
(58) Field of Search .............................. 204/422, 400, 204/404, 424, 431

(56) References Cited

U.S. PATENT DOCUMENTS

| | | | |
|---|---|---|---|
| 5,043,053 A | 8/1991 | Indig et al. | 204/421 |
| 5,192,414 A | 3/1993 | Indig et al. | 204/400 |
| 6,222,307 B1 | 4/2001 | Roy et al. | 313/326 |
| 6,357,284 B1 | 3/2002 | Kim et al. | 73/86 |

Primary Examiner—Alex Noguerola
(74) Attorney, Agent, or Firm—Nixon & Vanderhye P.C.

(57) ABSTRACT

A sensor for use in monitoring electrochemical potentials, includes (a) a crucible made of ceramic material having a closed end and an open end, the close end containing metal/metal oxide powder mixture retained therein by mineral insulating packing, the open end having a metallized band fired in the ceramic material; (b) an annular metal sleeve formed of a metal exhibiting a coefficient of thermal expansion compatible with the crucible, and having a distal open end brazed to the open end of the crucible, and a proximal open end; (c) an insulated electrical conductor having a distal end in electrical connection with the metal/metal oxide powder and extending through the mineral insulation packing and into the first annular sleeve, and having a proximal end terminating near the proximal open end of the annular sleeve; and (d) a signal transfer assembly sealingly associated with the proximal end of the annular sleeve including an electrical cable connected to the electrical conductor.

19 Claims, 1 Drawing Sheet

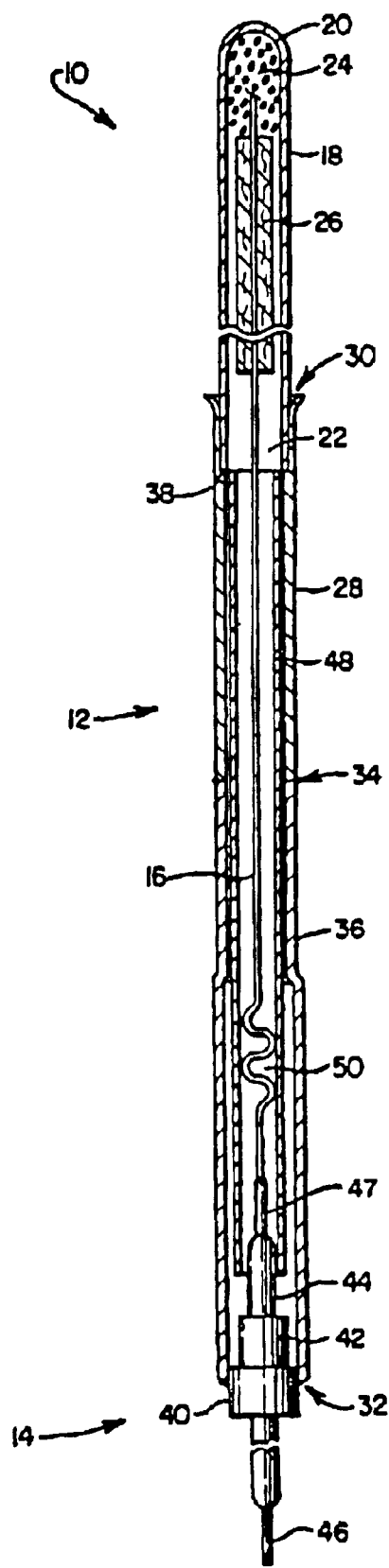

CERAMIC ELECTROCHEMICAL CORROSION POTENTIAL SENSOR PROBE WITH INCREASED LIFETIME

BACKGROUND OF THE INVENTION

Many nuclear reactors are typically constructed as boiling water reactors where suitable nuclear fuel is disposed in a reactor pressure vessel in which water is heated. The water and steam are carried through various components and piping which are typically formed of stainless steel, with other materials such as alloy 182 weld metal and alloy 600 used for various components directly inside the reactor pressure vessel.

Materials in the reactor core region are susceptible to irradiation assisted stress corrosion cracking. This is because the material in the core region is exposed to the highly oxidizing species generated by the radiolysis of water by both gamma and neutron radiation under normal water chemistry conditions, in addition to the effect of direct irradiation assisted stress corrosion cracking. The oxidizing species increases the electrochemical corrosion potential of the material, which in turn increases its propensity to undergo intergranular stress corrosion cracking or irradiation assisted stress corrosion cracking.

Suppression of the oxidizing species carried within such materials is desirable in controlling intergranular stress corrosion cracking. An effective method of suppressing the oxidizing species coming into contact with the material is to inject hydrogen into the reactor water via the feedwater system so that recombination of the oxidants with hydrogen occurs within the reactor core.

This method is called hydrogen water chemistry and is widely practiced for mitigating intergranular stress corrosion cracking of materials in boiling water reactors. When hydrogen water chemistry is practiced in a boiling water reactor, the electrochemical corrosion potential of the stainless steel material decreases from a positive value generally in the range of 0.060 to 0.200 V (Standard Hydrogen Electrode Potential, or "SHE") under normal water chemistry to a value less than −0.230 (SHE). When the electrochemical corrosion potential is below this negative value, intergranular stress corrosion cracking of stainless steel can be mitigated and its initiation can be prevented.

Considerable efforts have been made in the past decade to develop reliable electrochemical corrosion potential sensors to be used as reference electrodes that can determine the electrochemical corrosion potential of operating surfaces of reactor components.

The typical electrochemical corrosion potential sensor experiences a severe environment in a view of the temperature of the water wall exceeding 288° C.; relatively high flow rates of the water up to and exceeding several m/s; and the high nuclear radiation in the core region.

A drawback of currently available sensors is that they have a limited lifetime in that some have failed after only three months of use while a few have shown evidence of operation for approximately six to nine months. Since many of the locations where these sensors are installed are inaccessible during plant operation, a lifetime of at least 24 months must be obtained to allow for continuous monitoring during the entire fuel cycle (fuel cycle length is plant-specific but can range between 12 months to 24 months).

The invention disclosed here is most closely associated with commonly owned U.S. Pat. Nos. 5,043,053 and 6,357,284. Of the various types of sensors currently available, one (as disclosed in the '053 patent) includes a ceramic probe packed with a mixture of metal and metal oxide powder. Predominant failure modes for this type of ECP sensor include degradation of the ceramic material (yttria partially-stabilized zirconia) and cracking and corrosive attack of, the ceramic-to-metal braze used to attach the ceramic material to the balance of the sensor assembly.

Accordingly, it is desired to develop an improved ceramic electrochemical corrosion potential sensor addressing the insufficient useful life.

BRIEF DESCRIPTION OF THE INVENTION

A ceramic electrochemical corrosion potential sensor is disclosed herein that includes a ceramic tube or crucible, constructed of, for example, magnesia partially-stabilized zirconia or yttria partially-stabilized zirconia. The tube or crucible has a closed end and an open end. The outer diameter of the open end of the crucible includes a platinum metallized band fired into the ceramic for brazing the tube to a first open end of a metal sleeve, thus forming a hermetic seal. A first conducting wire extends from the mixture of metal and metal oxide powder through the ceramic tube to the second end of the metal sleeve. The second end of the sleeve is welded to and closed by, a metal adapter or connector (also referred to as a signal transfer assembly) that connects the conducting wire to a metal coaxial cable.

More specifically, the ceramic tube or crucible contains a mixture of high purity metal and metal oxide powders ($Fe/Fe_3O_4$, $Cu/Cu_2O$, or $Ni/NiO$). A high purity metal wire (Fe, Cu, or Ni depending on metal/metal oxide powder used) is secured in the center of this mixture. Crushed zirconia felt is packed around the center wire and on top of the metal/metal oxide powder mixture. Further, high purity glass wool is wrapped around and pressed on top of the crushed zirconia felt. The crushed zirconia felt and the glass wool provides structural integrity to the metal/metal oxide powder mixture and helps maintain its location inside of the closed end of the ceramic tube.

The ceramic tube or crucible is brazed to a first open end of a metal sleeve preferably constructed of a nickel alloy or other similar metal with a coefficient of thermal expansion that closely matches the coefficient of thermal expansion for magnesia partially-stabilized zirconia, or yttria partially-stabilized zirconia. The brazing process uses a braze alloy in an otherwise conventional practice that melts the braze alloy and forms a hermetic seal between the metal sleeve and the ceramic tube in the region where the ceramic tube has been metallized with platinum.

The second open end of the metal sleeve is sealed by an adapter also made of stainless steel or other equivalent metal. This sleeve serves as a transition piece so that the sensor body can be welded to a coaxial cable with a stainless steel outer sheath. The coaxial cable may be mineral insulated with magnesia oxide or another suitable insulator surrounding the center wire. The coaxial cable may be terminated in a suitable electrical connector or may be sealed through the use of a suitable epoxy with the center wire allowed to extend a small distance beyond the termination point of the coaxial cable.

Thus, in one aspect, the invention relates to a sensor probe for use in monitoring electrochemical potentials that includes (a) a crucible made of ceramic material having a closed end and an open end, the closed end containing metal/metal oxide powder mixture retained therein by mineral insulation packing, the open end having a metallized band fired in the ceramic material; (b) an annular metal sleeve formed of a metal exhibiting a coefficient of thermal expansion compatible with the crucible, and having a distal open end brazed to the open end of the crucible, and a proximal open end; (c) an insulated electrical conductor having a distal end in electrical connection with the metal/metal oxide powder and extending through the mineral insulation packing and into the first annular sleeve, and having a proximal end terminating near the proximal open end of the annular sleeve; and (d) a signal transfer assembly sealingly associated with the proximal end of the annular sleeve including an electrical cable connected to the electrical conductor.

In another aspect, the invention relates to a sensor probe for use in monitoring electrochemical potentials comprising a crucible having a closed end and an open end, the crucible constructed of magnesia partially-stabilized zirconia or yttria partially-stabilized zirconia, the open end having a band of platinum particles embedded in the crucible; a metal/metal oxide powder mixture retained in the crucible; a sleeve having one end brazed to the open end of the crucible; a conductor in electrical connection with the metal/metal oxide powder mixture and extending into the sleeve; and a signal transfer assembly sealed in an opposite end of the sleeve, and including a second conductor electrically connected to the first conductor.

The invention will now be discussed in detail in connection with the drawing described below.

BRIEF DESCRIPTION OF THE DRAWINGS

FIG. 1 depicts in cross-sectional elevation view the sensor probe of the present invention.

DETAILED DESCRIPTION OF THE INVENTION

Referring to the drawing, the structure of the sensor probe includes four principal components: an electrode 10, an annular support sleeve assembly 12, a signal transfer assembly 14, and an electrical conductor 16. The electrode 10 includes a zirconia tube or crucible 18 that has a closed end 20 and an open end 22. The zirconia tube 18 desirably is partially stabilized, e.g., with about 8.0% by weight magnesia, but it could also be partially-stabilized with about 8.0% by weight yttria. The ceramic tube is preferably formed by extrusion, hot isostatic pressing or a similarly suitable ceramic forming technique. The closed end 20 of the tube 18 is packed with a mixture 24 of metal/metal oxide powder.

The mixture 24 includes high purity metal and metal oxide powders ($Fe/Fe_3O_4$, $Cu/Cu_2O$, or $Ni/NiO$). The conductor 16, preferably a high purity metal wire (Fe, Cu, or Ni), is secured in the center of this mixture. A mineral insulation packing 26, e.g., crushed zirconia felt, is packed around the conductor wire 16 and on top of the metal/metal oxide powder mixture 24. The packing 26 may also contain high purity glass wool wrapped around and pressed on top of the crushed zirconia felt. The crushed zirconia felt and the glass wool packing will provide structural integrity to the metal/metal oxide powder mixture 24 and will help maintain its location inside of the closed end of the ceramic tube or crucible 18. The mineral insulating packing 26 not only maintains the metal/metal oxide powder 24 within the ceramic tube 18, but also electrically isolates the metal/metal oxide powder 24 from contact with other metal housing components of the probe structure. Additionally, after having packed the tube 18 with metal/metal oxide powder 24, the packing 26, when inserted in opening 22, wipes the interior surface of crucible 18 of any metal/metal oxide powder adhering to the interior walls.

The supporting sleeve assembly 12 includes an annular metal sleeve. While sleeve assembly 12 could be fabricated to include a single sleeve 28, it also is possible to employ two abutting sleeve components as shown in the drawing. Specifically, the first annular metal sleeve component 28, having a distal open end 30, is welded at juncture 34 to a second annular metal sleeve component 36 having a proximal open end 32. Sleeve 28 desirably is manufactured from a material, e.g., a nickel alloy or other similar material, that exhibits a coefficient of thermal expansion that is compatible with the ceramic material forming the tube 18. The material of construction for annular transition sleeve 36 preferably is stainless steel for providing corrosion resistance and minimizing costs associated to fabrication of the sensor probe of the present invention. The welding of sleeve 28 to sleeve 36 may be done in accordance with conventional tungsten inert gas (TIG) or other suitable welding techniques. The distal end 30 of sleeve 28 has a land 38 supporting the open end 22 of tube 18.

Since the joining of tube 18 to sleeve 28 should provide a hermetic seal, appropriate dimensional tolerances are maintained so that a snug fit between the proximal open end 22 of tube 18 and the distal open end 30 of sleeve 28 is maintained. The outer diameter at the open end of the ceramic tube 18 is metallized with platinum for a width of approximately 0.100 inches. This is achieved by firing the Platinum particles in the ceramic during the "green" stage of forming the ceramic (as understood by those skilled in the art), to form a metallized "band" about the open end of the tube 18.

The brazing process utilizes a brazing alloy and standard brazing process to melt the braze alloy and form a hermetic seal between the metal sleeve 28 and the ceramic tube 18 in the region where the ceramic has been metallized with platinum around its outer diameter.

The signal transfer or adapter assembly 14 is positioned within the proximal opening 32 of sleeve 36. This assembly 14 may include a stainless steel collar 40 that is welded to sleeve 36, such as by TIG welding, to provide a hermetic seal. Ceramic support 42, inwardly adjacent to collar 40, serves as an electrical connection from the outside to the interior of the electrode probe. Specifically, an insulated retainer 44 houses a nickel tube which is connected at its proximal end to coax cable 46 and to its distal end to the electrical conductor 16 via conductor 47. The signal transfer assembly 14 is commercially available and marketed, for example, by Reuter-Stokes Inc., a wholly owned subsidiary of the General Electric Company, in Twinsburg, Ohio. Should the tube 18 fail, water containing radioactive material will not leak to the outside by virtue of the seal provided by the connection of the collar 40 to the sleeve 36.

The final component, conductor 16, has a distal end bent into a hook or ring-like configuration which is pushed near but not touching the closed end 20 of the ceramic tube 18 (not shown in the drawing). The packing of metal/metal oxide powders 24 about the conductor 16 provides good electrical contact therebetween. Electrical conductor 16 then passes through the packing 26 and out of the open end 22 of tube 18 into the space provided within the annular sleeves 28 and 36. While the conductor 16 can be clad with ceramic insulation, preferably, an annular ceramic sleeve 48 (made of alumina, for example) is nested within the annular sleeves 28 and 36 and electrically insulates the conductor 16 from the metallic housing of the probe. A stress relief section 50 is incorporated into conductor 16 for insuring that the electrical connector is protected against conductor breakage by allowing for expansion and contraction of conductor 16 during heating and cooling cycles. The electrical conductor 16 terminates at a proximal end where it is welded to the conductor 47 projecting from the nickel tube 44 provided within the assembly 14. Conductor 16 may be formed of a material selected from the group consisting of iron, copper, or nickel depending on which metal/metal oxide powder is used.

It will be appreciated that the components described preferably are cylindrical in shape, though other shapes may be used. For example, tube 18, sleeves 28 and 36, and insulator 48 can be square, hexagonal, or of other geometric configuration.

With respect to performance specifications of the inventive reference electrode probe, the probe is designed to operate at temperatures ranging up to about 600° F. and pressures of up to about 2,000 psi. The electrode should exhibit a voltage that is within ±0.020 volts of the theoretical value for the metal/metal oxide/zirconia electrode sensor used in constructing the probe. The electrode probe sensor is capable of measuring ECPs to within ±0.010 volts in constant water chemistry.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A sensor probe for use in monitoring electrochemical potentials, comprising:
   (a) a crucible made of ceramic material having a closed end and an open end, the closed end containing metal/metal oxide powder mixture retained therein by mineral insulation packing, said open end having a metallized band comprised of platinum particles fired in the ceramic material;
   (b) an annular metal sleeve formed of a metal exhibiting a coefficient of thermal expansion compatible with said crucible, and having a distal open end brazed to said open end of said crucible, and a proximal open end;
   (c) an insulated electrical conductor having a distal end in electric connection with said metal/metal oxide powder and extending through said mineral insulation packing and into said first annular sleeve, and having a proximal end terminating near the proximal open end of said annular sleeve; and
   (d) a signal transfer assembly sealingly associated with said proximal end of said annular sleeve including an electrical cable connected to said electrical conductor.

2. The sensor probe of claim 1 wherein said electrical conductor is insulated by an annular electrical insulator housed within said annular metal sleeve.

3. The sensor probe of claim 2 wherein said annular electrical insulator is formed of alumina.

4. The sensor probe of claim 1 wherein said signal transfer assembly includes a metal collar welded to the proximate open end of said sleeve.

5. The sensor probe of claim 1 wherein said sleeve comprises first and second sleeve components, said first sleeve component brazed to said open end of said crucible, and said second sleeve component interposed between said first sleeve component and said signal transfer assembly, said second sleeve component being formed of a different material than said first sleeve component.

6. The sensor probe of claim 5 wherein said first sleeve component is formed of iron-nickel alloy, and said second sleeve component is formed of stainless steel.

7. The sensor probe of claim 1 wherein said electrical conductor is a wire formed of a material selected from the group consisting of iron, copper, and nickel.

8. The sensor probe of claim 1 wherein zirconia in said zirconia tube is partially-stabilized with approximately 8.0% by weight magnesia.

9. The sensor probe of claim 1 wherein zirconia in said zirconia tube is partially-stabilized with approximately 8.0% by weight yttria.

10. A sensor probe for use in monitoring electrochemical potentials, comprising:
    (a) a crucible having a closed end and an open end, said crucible constructed of magnesia partially-stabilized zirconia or yttria partially-stabilized zirconia, said open end having a band of platinum particles embedded in said crucible;
    (b) a metal/metal oxide powder mixture retained in said crucible;
    (c) a sleeve having one end brazed to the open end of the crucible;
    (d) a conductor in electrical connection with said metal/metal oxide powder mixture and extending into said sleeve; and
    (e) a signal transfer assembly sealed in an opposite end of said sleeve, and including a cable electrically connected to said conductor.

11. The sensor probe of claim 10 wherein said metal/metal oxide powder mixture comprises powders selected from the group consisting essentially of $Fe/Fe_3O_4$, $Cu/Cu_2O$ and $Ni/NiO$.

12. The sensor probe of claim 11 wherein a mineral insulation packing material is wrapped around the conductor on top of the metal/metal oxide powder mixture.

13. The sensor probe of claim 12 wherein said mineral insulation packing comprises crushed zirconia felt.

14. The sensor probe of claim 10 wherein said sleeve is comprised of a metal with a coefficient of thermal expansion substantially equal to a coefficient of thermal expansion of said crucible.

15. The sensor probe of claim 10 wherein said band has a width of about 0.100 inch.

16. The sensor probe of claim 10 wherein said sleeve comprises first and second sleeve components, said first sleeve component brazed to said open end of said crucible, and said second sleeve component is interposed between said first sleeve component and said signal transfer assembly, said second sleeve component being formed of a different material than said first sleeve component.

17. The sensor probe of claim 16 wherein said first sleeve component is formed of iron-nickel alloy, and said second sleeve component is formed of stainless steel.

18. The sensor probe of claim 10 wherein said electrical conductor is a wire formed of a material selected from the group consisting of iron, copper, and nickel.

19. The sensor probe of claim 10 wherein zirconia in said zirconia tube is partially-stabilized with approximately 8.0% by weight magnesia or 8.0% by weight yttria.

* * * * *

UNITED STATES PATENT AND TRADEMARK OFFICE
CERTIFICATE OF CORRECTION

PATENT NO.    : 6,869,511 B2  Page 1 of 1
DATED         : March 22, 2005
INVENTOR(S)   : Jett et al.

It is certified that error appears in the above-identified patent and that said Letters Patent is hereby corrected as shown below:

Column 5,
Line 48, "electric connection" should read -- electrical connection --

Signed and Sealed this

Fifth Day of July, 2005

JON W. DUDAS
*Director of the United States Patent and Trademark Office*